United States Patent [19]

Frazier

[11] Patent Number: 5,294,909
[45] Date of Patent: Mar. 15, 1994

[54] RESISTIVE SENSOR FOR POSITION DETECTION OF MANIFOLD FAILURES

[75] Inventor: Glenn E. Frazier, Roscoe, Ill.

[73] Assignee: Barber-Colman Company, Loves Park, Ill.

[21] Appl. No.: 1,365

[22] Filed: Jan. 7, 1993

[51] Int. Cl.⁵ .......................... H01C 3/04; H01C 3/06
[52] U.S. Cl. ..................................... 338/26; 338/214; 374/114
[58] Field of Search .................. 338/26, 214; 324/519; 219/505; 374/114, 110

[56] References Cited

U.S. PATENT DOCUMENTS 3,406,389 10/1968 Nailen .
3,540,041 11/1970 Payne .

OTHER PUBLICATIONS

"Continuous Fire & Overheat Detection System", Fenwal Incorporated Jan. 1989 publication No. 4.110.B IM.
"The Fenwal Discrete, Continuous Fire and Overheat Detection System", Fenwal Incorporated May 1985 pulbication No. MC 385.
"Continuous Fire and Overheat Detection Systems for Industry", Fenwal Incorporated Mar. 1991 publication No. 4.11.7 R1.
"The Kidde Connection", Walter Kidde Feb. 1989 publication No. A-802-R2-2.

Primary Examiner—Marvin M. Lateef
Attorney, Agent, or Firm—Leydig, Voit & Mayer

[57] ABSTRACT

An elongate resistive sensor useful as an element of a pneumatic manifold failure detecting and locating system. A sensing loop is based on a coaxial cable having a core of known resistance per unit length. A eutectic salt impregnated insulant separates the core and sheath but has a temperature breakdown characteristic which provides the sensing function. Upon a pneumatic manifold failure, the sensing cable is heated, the eutectic salt insulator breaks down, a core-to-sheath short occurs, and currents in the sensing cable are substantially altered as a result. The cable is connected as a loop, and differential currents into the ends of the loop are detected and processed to determine the position of the short. Terminating resistors are associated with connectors which connect multiple cable sections into a single loop, and the terminating impedance is further sensed to determine an open circuit condition at any connector.

12 Claims, 7 Drawing Sheets

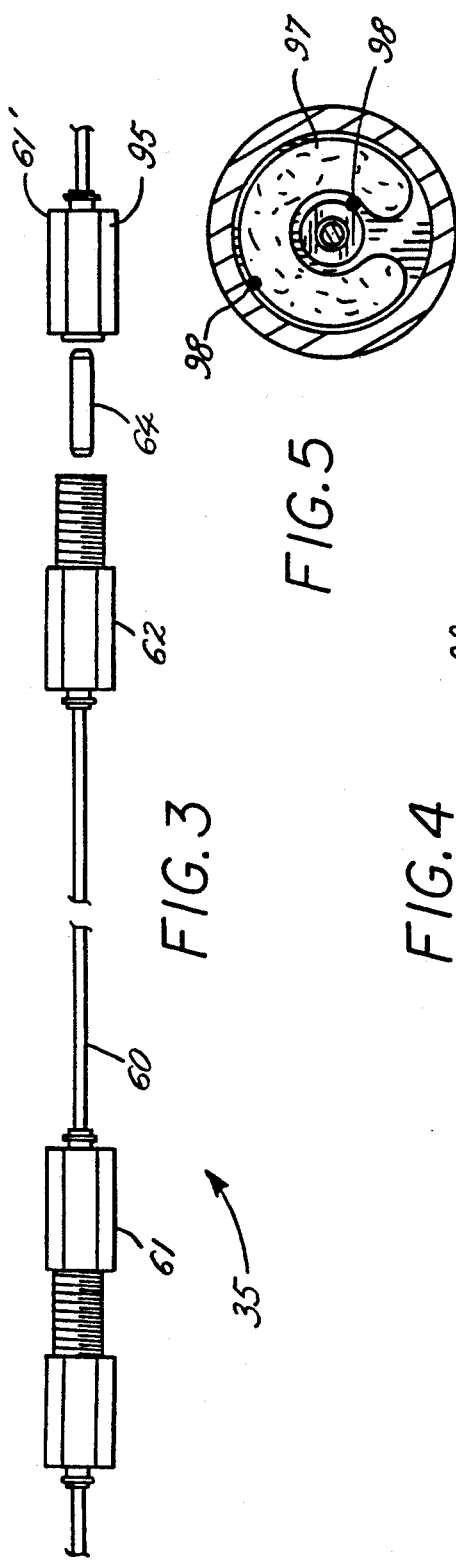

RESISTIVE SENSOR FOR POSITION DETECTION OF MANIFOLD FAILURES

FIELD OF THE INVENTION

This invention relates to heat sensors for aircraft, and more particularly, to a sensor for a manifold of an aircraft engine to assist in locating the position of leaks of engine bleed air in manifolds and ducting.

CROSS-REFERENCE TO RELATED APPLICATION

This invention is related to commonly owned application in the names of Glenn Frazier, John Goldsberry and John Krier III and entitled SYSTEM AND METHOD FOR LOCATING MANIFOLD FAILURES, filed concurrently herewith. The related application discloses a system which utilizes a sensor according to the present invention, the system being capable of signaling the occurrence and determining the location of pneumatic manifold leaks. The system is described generally in this application, and in greater detail in the co-pending application. To the extent additional detail on the structure of the system is needed for an understanding of the present invention, the disclosure of said co-pending application is hereby incorporated by reference.

BACKGROUND OF THE INVENTION

The jet turbine engine which powers modern aircraft is a device which relies for its operation on creating and utilizing high pressure gas streams. A compressor section, at the inlet of the engine, compresses external air, creating hot high pressure air. Most of that hot high pressure air is mixed with fuel in a combustor and burned, thus creating energy for propelling the aircraft. Some of the high pressure air can also be bled off for other purposes, such as cabin pressurization and anti-icing of leading edges. To meet these requirements, the modern jet turbine engine will typically be found to have an array of ductwork or manifolds which conduct the high pressure air to the locations where it is required.

The temperature of the gas can reach 1000° F. or more, and manifold or duct failures are not uncommon. A failure in the manifold or duct can also damage other nearby sheet metal or components. The engine itself is usually encased in a shroud, and sometimes located in a relatively complex compartment in the tail of the aircraft or in a pylon mount. Thus, it is not an easy matter to visually inspect the engine and its ductwork for evidence of gas leakage. Systems have therefore been devised for monitoring the areas around or near the gas turbine engine to sense and enunciate the occurrence of any leaks. It is also an aid to the flight crew to have some information on the location of the leak. For example, if the tail engine has developed a leak in the manifold, it is useful to know whether it is in the left or right side manifold, and action can be taken by the flight crew to continue to utilize the engine while avoiding pumping of hot air through the failed manifold section. It is also a benefit to the ground maintenance crew to be able to interrogate a monitoring system to determine with greater precision the location of any leaks, so that repairs and inspections can be made in an expeditious manner. To simply know that a leak has occurred, without more, might cause the ground crew to completely inspect extensive areas on and around the engine. With an automatic monitoring system, however, if the system were capable of reliably identifying the approximate position of all sensed leaks, maintenance personnel would then only need to inspect and repair those portions of the ducting which were known to have failed.

Systems have been proposed in the past for performing remote monitoring. Long cable-like sensors are associated with the manifold, and monitored by an automatic system in an effort to accomplish these goals. One type of elongate cable sensor is of the thermistor variety where a coaxial metallic cable of substantially zero resistance has a thermistor-type insulant separating a central conductor from an outer jacket. When the cable is heated over a reasonable portion thereof, the thermistor-type insulant material changes characteristics indicating the fact of a failure. The location of the failure is not quite so readily indicatable, however. A further limitation with this type of device is the fact that a rather large segment of the cable must be heated in order for the thermistor-type insulant material to perform its function, making it difficult to identify or pinpoint small localized leaks.

It has also been proposed to use a coaxial cable, which is like the thermistor cable in that both the jacket and shield have essentially zero resistance, but the separator material has a capacitance which changes after it is heated to a predetermined temperature. A capacitance bridge can monitor this type of cable and attempt to determine the position of localized heated portions of the cable. However, such an approach suffers from the difficulties of operating a capacitive bridge, including the interference effects which can arise from electromagnetic interference generated by other equipment in the aircraft. Another potential problem is electromagnetic interference generated by the system itself in operating the capacitance bridge at frequencies adequate to perform the necessary sensing.

Thus, while systems have been proposed which are theoretically capable of performing the monitoring function for locating localized leaks in aircraft pneumatic manifolds, those systems and their associated sensing cables have not been entirely satisfactory.

SUMMARY OF THE INVENTION

In view of the foregoing, it is an aim of the present invention to provide a sensor for a leak detection system for a pneumatic manifold in an aircraft which operates on simple resistance bridge principles.

In accomplishing that aim, it is an object of the present invention to provide a sensor cable for locating leaks in a pneumatic manifold which utilizes a eutectic salt impregnated insulant and coaxial conductors, one of which has a known and measurable resistance per unit length. It is a feature of such a sensing cable that it can be configured in a loop driven from its respective ends in such a way that the voltage or current drawn by the cable can be used not only to indicate the fact of a leak, but also to locate the leak with reliability and precision.

It is a further feature that the cable is configured in a loop with both ends of the loop connected to the controller, and in which the length of the loop can be varied to suit a particular application, with the sensing system able to automatically calibrate or compensate for various loop lengths.

It is a detailed object of the invention to provide such a system utilizing a resistive sensing element so as to minimize the effects of electromagnetic interference.

It is a further feature of the invention to provide a sensor which is useful with a differential current sensing technique for determining the exact location along the cable of the portion of the cable which has sensed a leak. In that respect, it is a feature of the invention that leaks can be located with an accuracy of approximately 3 or 4 inches in a sensor which may be on the order of 20 or more feet in length.

It is a feature of the invention that the resistive sensing cable has a known and measurable resistance per unit length, that the sensor is driven from both ends so that the differential current sensed at the ends of the cable can be used to determine with reasonable precision the location of any leaks sensed by the sensing cable.

It is a further feature of the invention that resistive sensing techniques are used which make the system more immune to electromagnetic interference than, for example, capacitive bridges.

It is a further feature of the invention that the sensing cable can be made up of a number of units connected end to end by reliable connector means, with resistances associated with the connector means, the system being adapted to sense the current change produced by the resistances as a result of a disconnected cable section, thereby to signal a break in the cable.

Other objects and advantages will become apparent from the following detailed description when taken in conjunction with the drawings, in which:

BRIEF DESCRIPTION OF THE DRAWINGS

FIG. 3 is a drawing showing a sensing cable constructed according to the present invention;

FIG. 4 provides further details on the connectors associated with the cable section;

FIG. 5 is an end view taken generally along the line 5—5 of FIG. 4 showing the internal cable connector resistance;

DETAILED DESCRIPTION OF THE PREFERRED EMBODIMENTS

Figure 1:
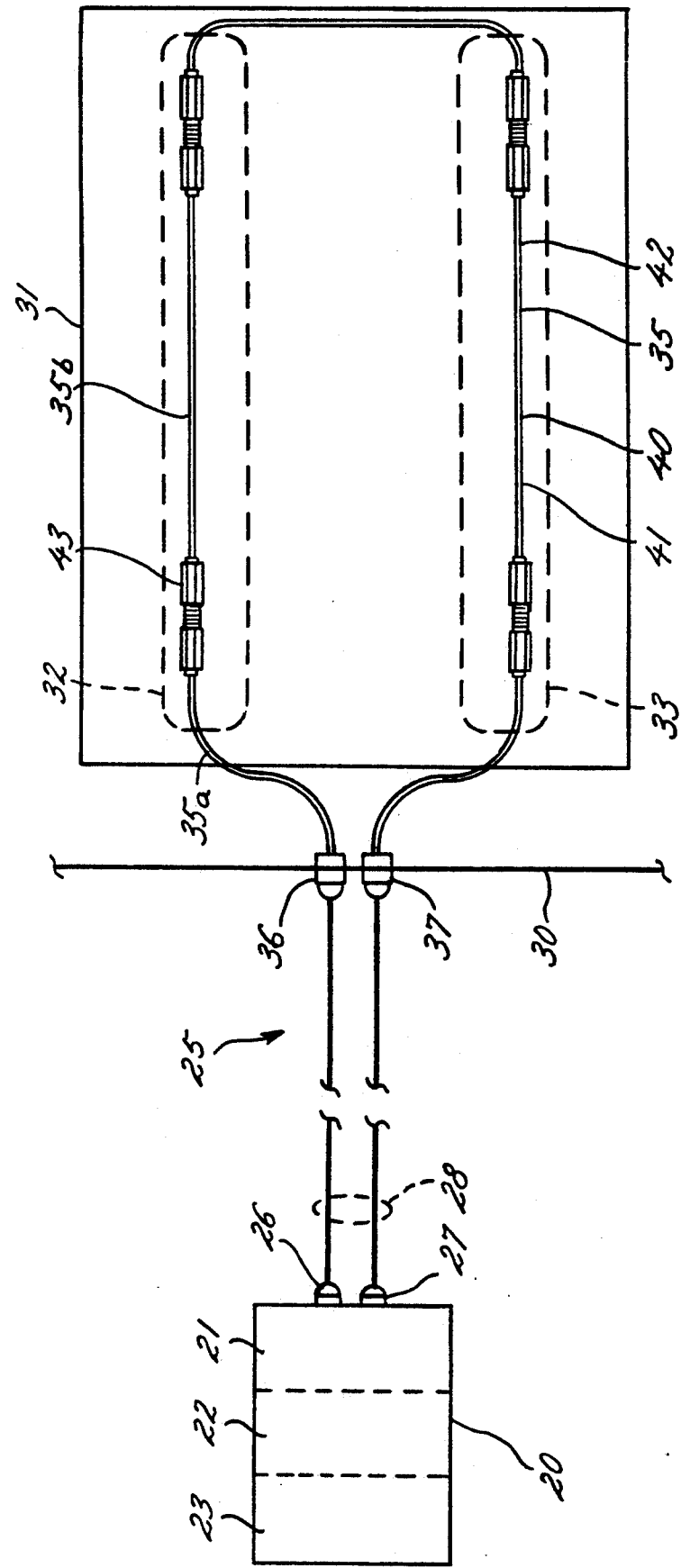
FIG. 1 is a sketch generally showing a pneumatic manifold failure detecting system, a sensing loop connected thereto, and associated with a schematically illustrated manifold on a gas turbine aircraft engine.

While the invention will be described in connection with certain preferred embodiments, there is no intent to limit it to those embodiments. On the contrary, the intent is to cover all alternatives, modifications and equivalents included within the spirit and scope of the invention as defined by the appended claims.

Turning now to the drawings, FIG. i shows, in greatly simplified and schematic form, a pneumatic manifold failure detecting system using a resistive sensor exemplifying the present invention. The system includes a central controller 20 having an analog section 21, a digital section 22, and a control section 23. The analog section 21 has connected thereto a plurality of sensor loops, one of such loops being generally shown at 25. In a practical implementation, it is preferred to provide capacity for approximately 14 sensor loops in a single controller. Connectors 26, 27 provide for connection of the respective ends of the loop to controller 20. A shielded cable 28 connects the controller to the area to be monitored. The cable 28 is intended to be of negligible resistance, such that the analog circuitry 21 within the controller 20 can operate in a differential current mode to sense resistance changes in the resistive temperature sensor which is used to monitor the engine manifold.

In the exemplary system, a bulkhead 30 separates the control components from an engine generally indicated at 31. The engine is shown as having a pair of manifolds 32, 33, which are intended to generically encompass the manifolds or ducting described above, which route the hot air from the engine 31 to associated points of utilization. The engine and manifold are not illustrated in any detail; the drawing is simply intended to demonstrate that the manifold occupies a substantial area, requiring a temperature monitoring sensor of substantial length in order to monitor the manifold for leaks which might occur anywhere along its rather substantial length. To that end, an elongate sensor cable 35 is provided having a pair of ends 36, 37 connected to the interconnecting wiring 28 and thence to the controller 20. The sensor loop 35 may be on the order of 12 feet for a rather compact installation, on the order of 22 feet in length for pylon mounted engines, and sometimes as long as 60 feet or more. The cable 35 is very long with respect to its diameter, its diameter typically being on the order of 1.8 millimeters.

The sensing cable 35, as will be described in greater detail below, has an outer metallic sheath 40 surrounding an inner conductor 41, with a eutectic salt impregnated insulant maintaining separation between the central conductor 41 and the sheath 40. In accordance with the invention, one of the metallic elements of the cable, preferably the core, has a defined and measurable resistance per unit length, such that the sensing of current flow into the cable can be utilized to determine the position in the cable at which a temperature fault has been sensed.

The eutectic salt impregnated insulant which fills the sheath 40 and maintains separation between the core 41 and the shield 40 is of the type which has a transition point or melts at a predetermined temperature. Upon melting, the melted eutectic salt functions like an electrical short to provide a localized core-to-sheath connection at the point of overheat. The core-to-sheath connection through the melted eutectic salt is often referred to as a short, for convenience. It will be appreciated, based on the development below, that the "short" can have resistance, and the term is used in that broader sense herein. The area of the cable which is overheated and can cause a eutectic salt short can be as small as one centimeter, and the controller 20 is adapted to sense the point along the cable 35 at which the short has occurred.

It will be seen that the loop 35 is associated with the manifold sections 32, 33, and can be affixed thereto such as by clips. Thus, if a manifold failure occurs at a given point, the cable 35 at that point will be locally heated, and the internal eutectic salt will melt to provide a localized short at that point. The controller 20 thereupon senses not only the fact of the short, but will utilize differential current sensing techniques to locate the position of the short, and provide an indication thereof.

For ease of manufacturing, assembly, and maintenance, the cable 35 is not provided as a continuous length custom fit device, but is made up of individual sections 35a, 35b, etc. Coaxial connectors 43 interconnect the sections 35a, 35b. Thus, the overall loop 35 has electrical continuity through the core and electrical continuity through the sheath, and the resistance of the core will depend on the total length of the loop. For example, in the preferred system, the resistance of the core material is selected to be approximately 15 Ohms per meter, and thus the overall resistance of the loop might be on the order of 50 to 100 Ohms.

As will be described in greater detail below, the analog section 21 of the controller 20 couples a signal to the sensing cable 35 and senses the differential current drawn by the cable. Whenever an overheat condition occurs due to a manifold failure, the eutectic salt at that portion of the cable will break down and cause a localized core to sheath short. The very high core-to-core sheath resistance which had existed theretofore then becomes less than 100 Ohms. Differential current sensing elements within the analog circuitry 21 measure the differential current drawn by the respective ends of the cable (to the short) and thereby determine the lengths of the cable to the short. The analog circuitry includes a multiplexer for scanning the sensor loops and outputting a sequence of signals relating to measurements from the respective loops. The digital circuitry 22 includes an analog-to-digital converter responsive to the signals coupled through the analog multiplexer, produces digital signals related to the differential current measurements, and assists in the determination of the location of a manifold failure, as will become more apparent. Upon determining the event of a failure and locating its position, the control circuitry 23 thereupon causes the information to be written into non-volatile memory recording the fact that a failure has occurred and the location of the failure.

As noted above, in the preferred embodiment of the invention, controller 20 controls multiple loops, and it is preferred that the loops be sensed in sequence utilizing analog multiplexing techniques which share a single analog-to-digital converter. The digital control circuitry 23 causes the scanning of each loop in turn and records any failures. Built-in-test circuitry within the digital controller also monitors the loops to assure their continuity, performs tests to determine overall loop resistance, and the like, all as will be described in greater detail below.

Figure 2:
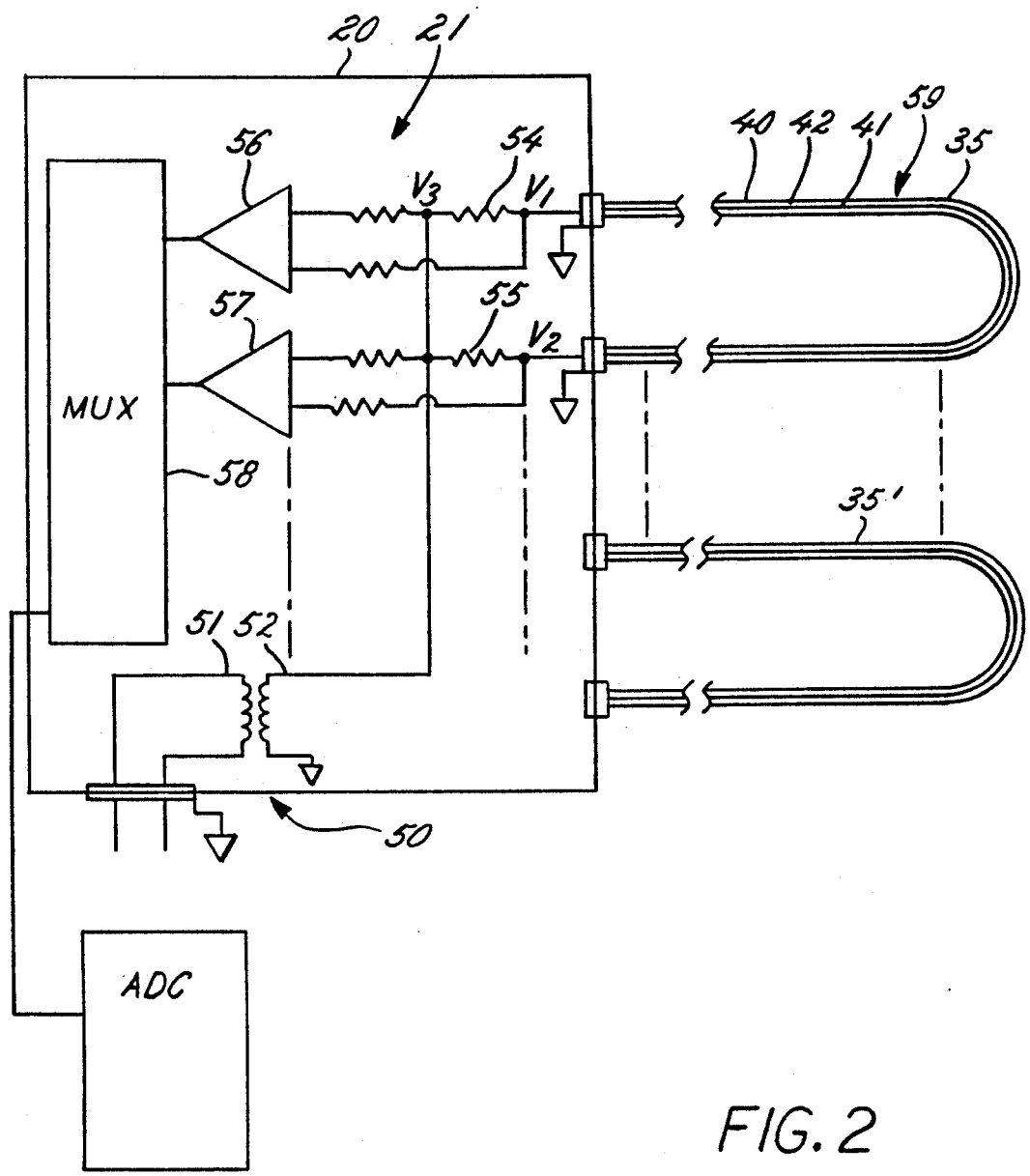
FIG. 2 is a very general schematic diagram illustrating the principles of operation of a pneumatic manifold failure detecting system utilizing a resistive sensing element exemplifying the present invention.

Turning now to FIG. 2, a brief description will be given of the general operation of the analog sensing system. FIG. 2 shows a pair of sensor loops 35, 35', with electrical circuitry shown only for the loop 35. Illustrated in the controller 20 are primarily the analog components 21 thereof. Before commencing a description of the sensing operation of the circuit, it will be recalled that the central conductor 41 of the cable 35 is separated from the sheath 40 by a eutectic salt insulator 42, and the insulator has a relatively high resistance at normal temperatures. It is configured to break down at a predetermined temperature, such as 400° F. At that temperature, the eutectic salt insulator 42 switches from a relatively high impedance to a relatively low impedance, causing a localized core 41 to sheath 4 short at the point at which the cable 35 had been overheated. It is the function of the analog portion 21 of the circuitry 20 to monitor the resistance of the sensor cable 35 to detect the change in resistance, and to utilize the differential current sensing capability of the circuitry 21 to locate the point on the cable 35 where the localized short has occurred. It will be kept in mind, of course, that the core 41 has a given resistance per unit length, such that the resistance measured from its respective ends will be an indication of the location in the cable where the localized short has occurred.

For driving the cable with a predetermined signal, the controller 20 includes a transformer 50 having a primary 51 driven from an external AC power source and a secondary 52 connected to the respective sensing cables 35, 35'. In the illustrated embodiment, one end of the secondary 52 is connected to an internal circuit common or ground, and the sheaths of all the cables 35, 35' are also connected to internal ground. The cores 41 are connected to the non-common end of the secondary winding 52. Focusing particularly on cable 35, it will be seen that the secondary 52 is connected to both ends of the core via sensing resistors 54, 55. When there is no localized short in the sensor loop 35, the resistance from core to sheath is relatively high (determined primarily by the terminating resistors to be described below), and there is very little current flow from the secondary 52 through the respective sensing resistors 54, 55. Differential amplifiers 56, 57 are connected across the respective sensing resistors 54, 55, and the outputs of those amplifiers are connected to an analog multiplexer 58. The multiplexer 58 in turn is controlled by the digital circuitry (not illustrated in FIG. 2) to sense the voltage drops across the respective sensing resistors 54, 55, and provide analog signals through the multiplexer 58 to an analog-to-digital converter. The ADC produces signals relating to the magnitudes of the voltages across the sensing resistors, and thereby provide an indication of differential current flow in the respective ends of the loop. In the absence of any manifold fault, the currents in the respective sensing resistors will be rather low and will be substantially equal.

Upon the occurrence of a manifold failure, a portion of the cable 35, such as indicted by the arrow 59, will be heated and cause a core to sheath localized short in the cable at that point. That localized short will cause an increase in current flow from the secondary 52 through the core 41 to the sheath and back to the secondary. Unless the short is at the mid-point of the sensor loop 35, the current flow through the respective sensing resistors 54, 55 will be unequal, because of the differing lengths of resistive core 4 encountered by the respective current paths. The amplifiers 56, 57 will continue to produce signals relating to the current flow through the sensing resistors 54, 55, and that differential current flow will be sensed by the digital circuitry of the controller 20. Utilizing relationships to be developed below, the controller 20 will determine the location of the point 59 along the sensor loop 35 at which the failure has occurred.

Attention will first be directed to the sensing cable itself. FIG. 3 shows a sensing cable illustrated generally at 35 including an elongate length 60 of coaxial cable terminated by connectors 61, 62. Connector 62 is considered to be the female connector, and connector 61 the male connector. A subsequent cable has a male connector 61' positioned to be mated with the connector 62 of the cable 60. A sleeve interconnect element 64 serves to provide electrical continuity between the cores of connected cable sections. A pair of assembled connectors are shown in greater detail in FIG. 4. Each of the cable sections has a core conductor 70, which in the preferred embodiment has a predetermined resistivity (or in other words, a predetermined resistance per unit length). Preferably, the core 70 is of a nickel alloy of a low temperature coefficient of resistance, and has a resistance of approximately 15 Ohms per meter. The central conductor 70 is surrounded by a coaxial shield 72, preferably of nickel, but having a substantially zero resistance, in other words, a resistance which is negligible with respect to the resistance of the central core 70. By zero resistance, it is intended to describe a material of ordinary conductivity (not a superconductor), and to distinguish from the resistive material having a measurable resistivity, such as 15 Ohms per meter. An insulator material 74 separates the core and cladding 70, 72 and typically provides a relatively high resistance between those elements. The insulator material 74 is preferably a eutectic salt which is specially configured to melt at the temperature at which the cable is to function. It is preferred to use an aluminum oxide insulant impregnated with a eutectic salt for the material 74. The nature of the eutectic salt is adjusted, according to known principles, to meet the temperature sensing requirements of the cable. It is presently desired to produce insulator materials 74 of two characteristics, one capable of responding at about 400° F., and another capable of responding at about 225° F. It will also be desirable to provide sensors with other response temperatures, for example, a sensor responsive at about 180° F. is contemplated. It is well within the skill of the art of those supplying such cable systems to configure the eutectic salt mixture in the aluminum oxide insulant to provide a breakdown temperature at a desired level.

Using known manufacturing techniques, the eutectic salt mixture 74 is compacted to a high degree so that the core 70 and shield 72 are maintained separated, even in the presence of relatively tight bends in the cable or in an environment which is exposed to vibration, such as would be encountered in an aircraft application. To better understand the dimensions involved, the overall outer diameter of the sheath 72 is about 1.8 millimeters, and its length around 7 meters. It is desired to make the cables as thin as possible so that it can be easily routed around the engine compartment and manifold, to provide for temperature response and yet provide minimum weight penalty to the aircraft. Typically, the eutectic salt insulator 74 is hygroscopic, and thus, after the material is highly compacted, the cable is sealed by a hermetic ceramic seal which prevents moisture ingress. It will be seen in FIG. 4 that the sheath 72 of the cable section at the left of the drawing is welded at 80 to a central metallic bushing 82. The metallic bushing 82, in turn, has a housing member 83 welded thereto and the housing member 83 holds a ceramic sealing insert 84. The central conductor 70 penetrates the ceramic seal 84, is surrounded by a metallic header 85 and welded thereto at the free end 85a. The header 85 fits snugly within the ceramic seal 84. Finally, an outer sleeve member 86 is welded to the bushing 82 at the end thereof, to provide protection for the header 85 and also to complete the seal, so that the insulant material 74 is protected from the ingress of moisture through the now-sealed header. FIG. 4 also shows the interconnecting member 64 having spring-loaded contacts 90 which engage the periphery of the header 85. They similarly engage the periphery of a header in the next sequential connector, similarly sealed. The difference between the two connectors, however, is that the connector illustrated fully in FIG. 4 shows the male connection with an outer ring 92 having a threaded insert 93 welded therein. The other or female connector has no outer ring 92 or threaded member 93, but instead simply has a hexagonal bushing 95 (see FIG. 3) threaded to engage the housing 93, to force the interconnecting sleeve into contact with the header portion 85' installed in a similar fashion in that connector. The details of that installation will not be further illustrated, as they will now be understood by those skilled in this art.

In summary, the sensor cable is constructed with a hermetically sealed sheath, preferably nickel, but can also use other heat-resistant materials such as the nickel-based alloy Inconel. In order to reduce weight while maintaining reliability, a sheath diameter of about 1.8 millimeters is preferred. A center conductor is produced from a material of known resistivity, such as Tophet A, a resistive element which is primarily nickel. This material has a very low temperature coefficient of resistance and a high tensile strength. The center conductor is formed to provide a resistance of about 15 Ohms per meter.

The sensor connectors are also made of nickel, and provide a hermetic ceramic seal. The ceramic-to-nickel seal is specifically designed to withstand the high temperatures in which the sensor is required to survive. Since the sheath and connector are made from substantially the same materials, the sensors will not have the corrosive or linear expansion problems which can occur with dissimilar materials.

It is also noted that the eutectic salt sensor has a distinct advantage over averaging type sensors, such as thermistor sensors. A thermistor sensor requires heating over a substantial area thereof in order to indicate a manifold leak. The present sensor, however, can detect a relatively small leak which heats only a 1 centimeter length of the sensor. An averaging sensor, such as a thermistor sensor, will not produce a sufficient resistance change when it is heated in such a small area. Accordingly, the sensor according to the present invention can detect relatively small manifold leaks because it has a dramatic change in resistance at any one point, interposing a localized electrical short at the point of overheat, without requiring a relatively large area to be heated in order to accomplish that result. The resistive center conductor allows the controller then to accurately and reliably locate the fault at any point along the sensor loop, and in all environmental conditions.

In accordance with one feature of the invention, means are provided for determining if one of the intercable connectors has been disengaged, and of determining which connector is open. To that end, each of the connector sections has a terminating resistance 97 associated therewith (see FIGS. 4 and 5). The terminating resistance 97 is preferably in the form of a washer-shaped ring (see FIG. 5) formed of a resistive material and laser trimmed in a U-shape to have a predetermined resistance. The resistance is selected to be relatively high as compared to the resistance of the core, preferably at least one order of magnitude greater. We currently prefer to use resistances 97 of about 34k Ohms. The terminating resistance is brazed at 98 to both the core and the shield, preferably around the entire inner and outer periphery of the resistor. Thus, the resistance 98 provides a high resistance core-to-shield connection at each connector. When a number of sections of cable, such as 5 or 6, are connected together, the paralleled terminating resistors will provide an overall core-to-shield resistance (in the absence of a heat-caused failure) which measured in parallel is at least an order of magnitude greater than the resistance of the core. The controller will sense the current flow resulting from that known impedance to determine the continuity of the sensor loop. If one of the connectors vibrates free, the core-to-shield impedance will change by virtue of the fact that some of the resistors 97 will be in one portion of the loop and others in the other portion. As will be described below, it will then be possible to utilize the differential current sensing into the now-opened loop to determine exactly which of the connectors has opened. The resistive sensing capabilities of the present invention thus not only provide the benefits set out at the outset, but in addition, when utilizing the connector terminating resistors as just described, provide yet another means for assuring reliability of the system or detecting system failures automatically and at the earliest possible time.

As a feature of the system, the resistive sensor, which may be of any length within practical limits, is utilized in a self-calibrating mode to determine the total loop resistance for the actual length of the sensor loop. In the past, self-calibration has not been a substantial problem, because the resistance of the conductors of the sensing loop was essentially zero, and therefore the total resistance of the loop was not pertinent. However, in accordance with the present invention, the loop resistance is the variable which is used to determine position of any failure, and thus total loop resistance is important. It was noted above that the loop can be configured with a number of sections of sensor cable connected together, and in carrying out the invention, the controller of the present invention performs a test on each loop to determine the total loop resistance. That total loop resistance is then used in the process for determining, based on differential current signals, where in the loop a manifold failure has occurred.

Figure 6:
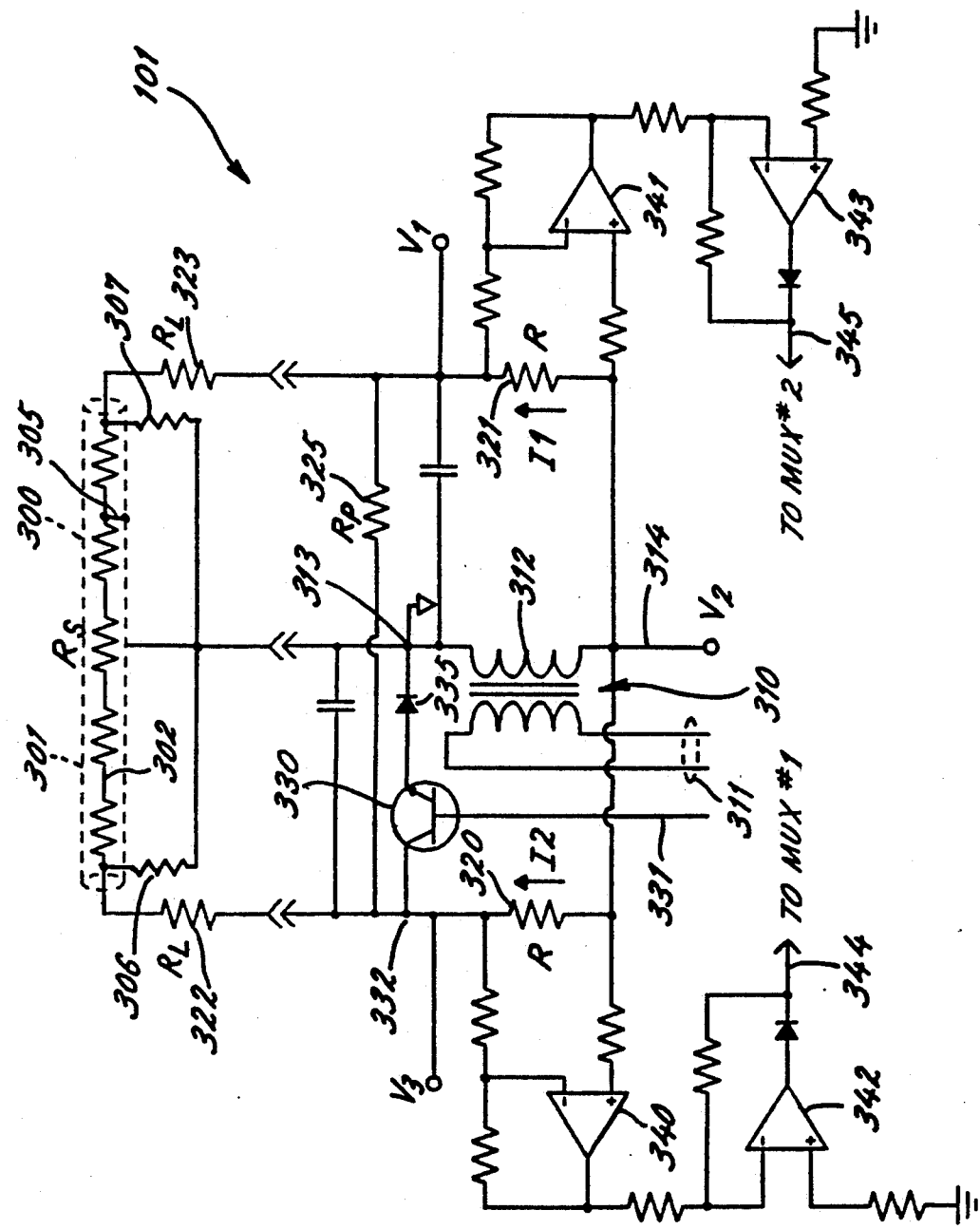
FIG. 6 is an equivalent circuit diagram showing the resistive sensing elements for one channel.

The manner in which the system determines the location of a fault will now be described. FIG. 6 illustrates the sensing loop for one channel having amplifier outputs to the common multiplexer. It will be understood that the circuitry of FIG. 6 is repeated for each channel, and that a single multiplexer receives all of the outputs. A sensing loop is shown at 300 and includes a sensor having a shield 301 and an inner resistive core 302. The resistive core 302 is illustrated as a distributed resistance, and it will be appreciated that heating of the cable 300 anywhere along its length will cause a breakdown of the eutectic salt insulator and a localized core-to-shield short such as that indicated by the dashed line 305. It is seen that except for the illustrated short 305 there are no connections within the sensor 300 between the core and shield, and that the eutectic salt maintains the core separated from the shield.

For purposes of sensing breaks between sections of the cable, it was noted above that connector resistors (sometimes called terminating resistors herein) are utilized, and those resistors are shown in FIG. 6 as resistors 306, 307 connected at section ends between the core and shield. If the sensor 300 were made up of additional sections, resistors would also be connected from core to shield at each of the sections. The resistors 306, 307 are on the order of 34K, and with the resistance of the cable being on the order of 15 Ohms per meter, it will be appreciated that the core resistance is insignificant with respect to the terminating resistances. It will also be understood that the terminating resistances can be considered to be in parallel when the cable is connected and continuous. Thus, if 5 sections of cable are utilized, for example, there would be 10 resistors 306, 307 in parallel between core and shield, and if each were of 34K, the total impedance presented by a cable (with no internal short) would be on the order of 3.4K Ohms.

The remainder of the circuitry shown in FIG. 6 is that associated with the analog channel, such as that illustrated at 21 in FIG. 1. The total resistance of the sensor is shown as $R_S$, and it is seen that a voltage is applied to the sensor by means of a transformer 310 having a primary 311 supplied by 115 volt, 400 Hz. cycle, and a secondary 312 having one input 313 connected to ground, and a second input 314 for driving the respective sensors. The sensor cable is driven from each end through current sensing resistors 320, 321. The resistors 320, 321 are precision resistors and it is the current through those resistors which is monitored to determine differential current flow into the loop. Load resistances ($R_L$) 322, 323 are also shown, and represent the resistance of the wiring connecting the sensing system to the loop. That resistance can be determined and input to the system, and will remain unchanged. A shunt resistance 325 having a magnitudinal $R_P$ is shown as shunting the sensor; resistance 325 represents the parallel impedance looking into the measuring circuitry. A transistor 330 is provided for use in the self-calibration mode, and that will be described later. Coupled across the sensing resistors 320, 321 are differential amplifiers 340, 341, respectively. Those amplifiers have appropriate weighting resistors and drive respective buffer amplifiers 342, 343 to produce single-ended outputs relating to the magnitude of the current through the sensing resistors 320, 321 which are coupled to the multiplexer by means of lines 344, 345.

It will be seen that the same voltage is applied to both ends of the sensing loop 300 by virtue of the fact that the secondary 312 of the transformer is connected from the shield through the respective sensing resistors 320, 321 to the respective ends of the sensing loop. Thus, when there is no short in the eutectic insulator (and ignoring the shunt terminating resistors 306, 307 for the moment), equal currents will be drawn through the sensing resistors 320, 321. The current will be at a relatively low level (on the order of a milliamp), and the system will be in balance. When a short such as 305 is in place, however, current will flow in the right-hand portion of the loop through the resistor 321 through the right-hand portion of the sensor resistor and to the shield through the shunt 305. A relatively small resistance, comprising perhaps only 1/5 of the total resistance $R_F$, will be interposed across the right portion of the loop, and the currents through resistor 321 will be relatively high. In the left-hand portion of the loop, the current through resistor 320, will be at a somewhat lower level, but again higher than it had been when the system was in balance. The currents through resistors 320 and 321, identified as $I_2$ and $I_1$ on the drawing will be measured as an indicator of the position of the short 305.

Figure 7:
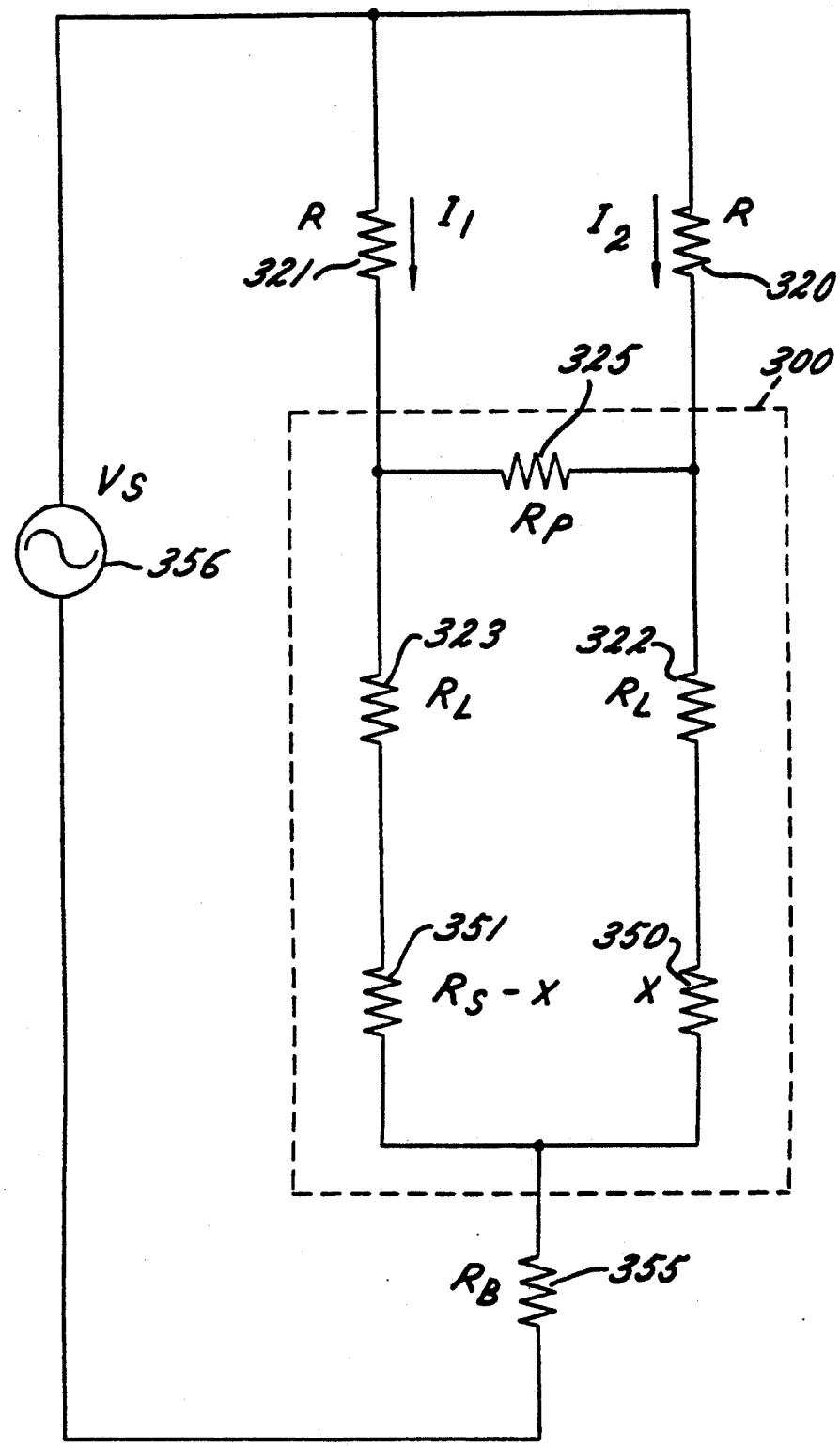
FIGS. 7 and 8 are simplifications of the circuit diagram of FIG. 6 useful in understanding a derivation of the position locating functionality of the present invention.

The manner in which that is accomplished will now be derived. The equivalent circuit for the sensor input circuitry shown in FIG. 6 is illustrated in FIG. 7 which shows the currents $I_1$ and $I_2$ through the resistors 320 and 321. The resistance of the sensor loop itself is shown in the rectangle indicated at 300. It includes the parallel shunt impedance 325, and the load resistance of the wiring 322, 323. FIG. 7 assumes that a localized short 305 has occurred, and a resistance X identified by the reference numeral 350 is intended to indicate the portion of the resistance of the sensor to the point of short through which the current $I_2$ flows. Similarly, the resistance 351 is indicated to have a value of $R_S$—X, and that is intended to indicate the resistance in the right-hand portion of the loop of FIG. 6, i.e., the resistance which will be seen by the current $I_1$ flowing through the sensing resistor 321. A resistance 355 identified as $R_P$ is intended to show the impedance of the eutectic salt which forms the short. The driving voltage is indicated at 356 and represents the voltage output by the secondary of the transformer 310.

Figure 8:
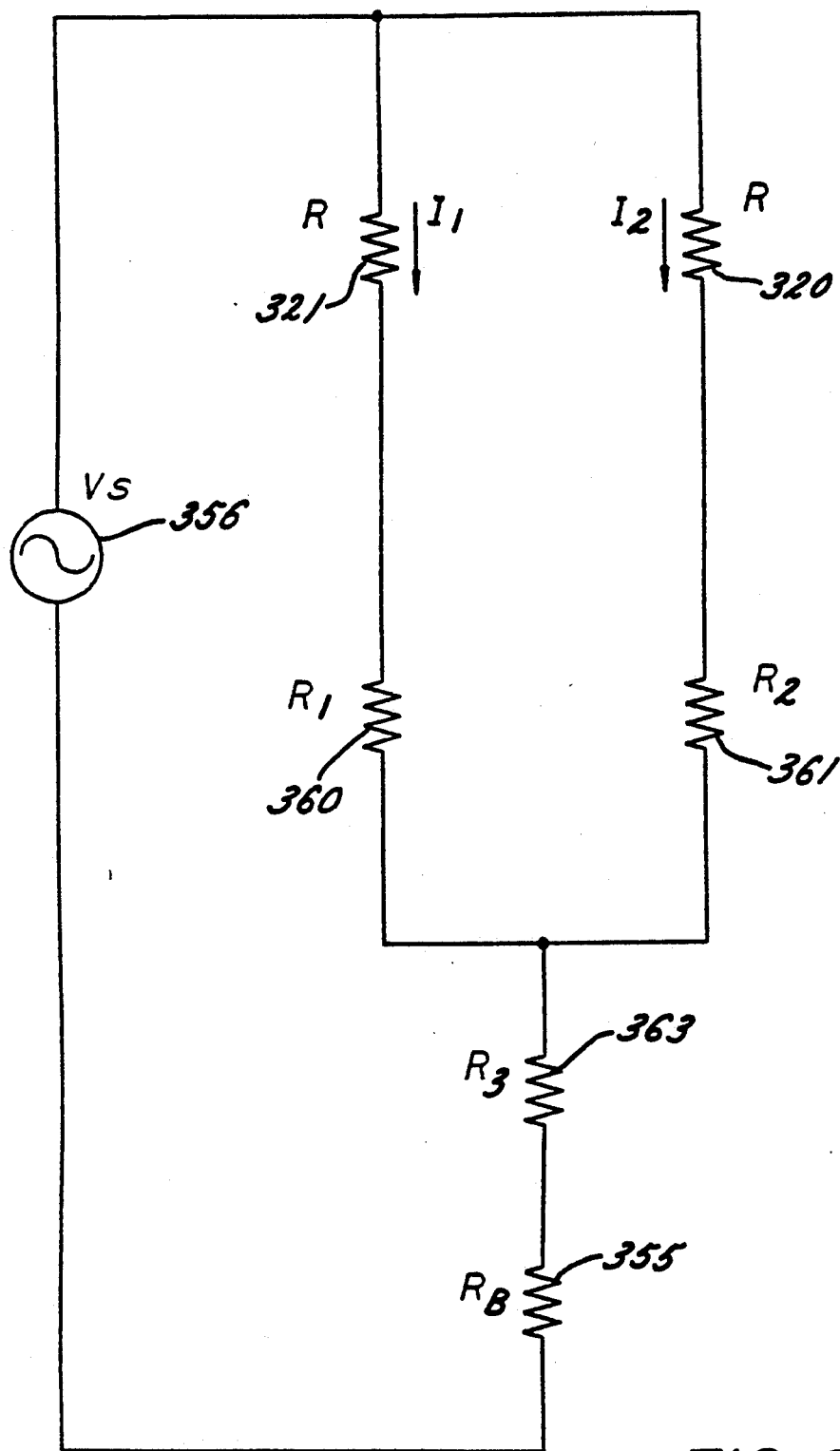

The circuit diagram of FIG. 7 can be simplified to the circuit diagram of FIG. 8 by a delta-to-wye conversion where:

$$R_1 = \frac{R_p(R_S - X + R_L)}{R_p + R_S + 2R_L} \quad (1)$$

$$R_2 = \frac{R_p(X + R_L)}{R_p + R_S + 2R_L} \quad (2)$$

$$R_3 = \frac{(X + R_L)(R_L + R_S - X)}{R_p + R_S + 2R_L} \quad (3)$$

Having made that conversion, the system of FIG. 8 can then be analyzed to determine relationships for determining the position of a localized short. FIG. 8 also shows the source voltage 356, the currents $I_1$ and $I_2$ through the respective sensing resistors 321, 320. The resistances $R_1$ and $R_2$, which have been developed in the expressions (1) and (2), are shown in the drawing and identified by reference numerals 360, 361. The resistance $R_3$ developed in expression (3) is identified by reference numeral 363. Finally, the impedance of the short itself $R_B$ is shown at 355.

The point on the sensor X where the breakdown has occurred can be found from the following derivation:

$$V_S = I_1 R + I_1 R_1 + (I_1 + I_2)(R_3 + R_B) \quad (4)$$

$$V_S = I_2 R + I_2 R_2 + (I_1 + I_2)(R_3 + R_B) \quad (5)$$

$$I_1 R + I_1 R_1 = I_2 R + I_2 R_2 \quad (6)$$

$$(I_1 - I_2)R = I_2 \left[ \frac{R_p(X + R_L)}{R_p + R_S + 2R_L} \right] - I_1 \left[ \frac{R_p(R_S - X + R_L)}{R_p + R_S + 2R_L} \right] \quad (7)$$

$$(I_1 - I_2)R(R_p + R_S + 2R_L) = \quad (8)$$
$$I_2 R_p X + I_2 R_p R_L - I_1 R_p R_S + I_1 R_p X - I_1 R_p R_L$$

$$X = \quad (9)$$
$$\frac{(I_1 - I_2)R(R_p + R_S + 2R_L) + I_1(R_p R_S) + (I_1 - I_2)(R_p R_L)}{(I_2 + I_1)R_p}$$

It will thus be seen that the equation for the point X is not dependent upon the excitation voltage $V_S$ or on the resistance of the insulation at the point of breakdown $R_B$. Because of this, fluctuations in the aircraft supply voltage, or voltage changes due to loads on the transformer, have no effect on determining the location of an overheat condition. Similarly, the actual impedance imposed by the shunt itself has no effect on the position determination.

The expression (9) does not take account of the terminating impedance interposed between core and sheath at each connector. Even though the terminating impedances are at least an order of magnitude greater than the core resistance, it is desirable to make an adjustment in the expression (9) to make it more exact with respect to the condition with terminating impedances in place. It has been found that the value for R, that is the value of the sensing resistor, can be adjusted slightly, based on empirical tests either with actual systems or simulated systems of the desired length and with the prescribed number of sections in place. The tests are performed to determine a value for R to be used in expression (9) which will give more accurate result and account for the terminating resistors. For example, typically a value R which is used in the circuit is 100 Ohms, and we have found that using an adjusted value for R in equation (9) empirically determined, of 104.86 Ohms in one case, and 110.22 Ohms in another case take account of the presence of the terminating resistors.

It will be seen from expression (9) that the position determination is based only on the respective currents (which have been measured), and on known impedances. The total impedance for the loop R is tested periodically, and is stored for use in the expression (9). The parallel impedance $R_P$ is known and is input for later use. Similarly, a value of $R_L$ can be input at the outset and need not be changed. Thus, it is only necessary to measure the currents I and I: (or voltages relating to those currents) and utilize those in expression (9) in the system microprocessor, and a result will be produced which is the actual position of the localized short. Utilizing practical components, the short can be located within about 3 inches in a short loop (12 feet or so) and within about 4 inches in a longer loop (or 22 feet or so). Better accuracy can be derived with greater precision in the A to D converter and in other components. It is currently believed that the precision of 3 inches or 4 inches is adequate for most purposes.

Referring again to FIG. 6, the transistor 330 will be seen to have a test signal coupled on a line 331 to the base thereof, so that during a test condition the transistor 330 is switched on to connect the point 332, (the upper portion of the sensing resistor 320) to circuit ground. Thus, the secondary 312 of the driving transformer 310 is connected across the core, since ground is connected to the left-hand end and the transformer terminal 314 to the right-hand end. The resistor 320 is bypassed, and all current through the loop flows through sensing resistor 321. It will thus be seen that the current $I_1$ through sensing resistor 321 during this test condition can be measured to determine a value for $R_S$, the total resistance of the loop. The actual manner in which that will be determined is demonstrated in the following expressions:

$$I_2 = \frac{V_S - V_X}{R} \quad (10)$$

$$I_1 = \frac{V_S - V_X}{R + \left[ \frac{(R_S + 2R_L)R_P}{R_S + 2R_L + R_P} \right]} \quad (11)$$

$$V_S - V_X = I_2 R \quad (12)$$

-continued $$V_S - V_X = I_1 \left[ R + \left( \frac{(R_S + 2R_L)R_P}{R_S + 2R_L + R_P} \right) \right] \quad (13)$$

$$I_1 \left[ R + \left( \frac{R_S + 2R_L)R_P}{R_S + 2R_L + R_P} \right) \right] = I_2 R \quad (14)$$

$$I_1 R + I_1 \left[ \frac{(R_S + 2R_L)R_P}{R_S + 2R_L + R_P} \right] = I_2 R \quad (15)$$

$$\frac{I_1 R_P}{(I_2 - I_1)R} = \frac{R_P + (R_S + 2R_L)}{R_S + 2R_L} \quad (16)$$

$$\frac{R_P}{\left[ \frac{I_1 R_P}{(I_2 - I_1)R} \right] - 1} = R_S + 2R_L \quad (17)$$

$$R_S = \left[ \frac{R_P}{\left[ \frac{I_1 R_P}{(I_2 - I_1)R} \right] - 1} \right] - 2R_L \quad (18)$$

The sensor resistance (which includes in the expression (18) the resistance of the wiring which connects the sensor to the system) is thus a function of current $I_1$ (the current through the sensing resistor 321) and of the current $I_2$ (which in turn is a measure of the drop across the turned-on test transistor 330 and its associated diode 335). Thus, the system is able to turn on the transistor 330 by means of an appropriate signal on line 331, to measure $I_1$ and $I_2$ (or the voltages which produce those currents), and utilizing the known impedances $R_P$ and $R_L$ to determine the actual resistance of the sensor loop. That resistance can be updated periodically and utilized in the expression (9) for determination of the actual point of a short caused by an overheat.

As in the case of the position determination, the expression (18) does not take account of the presence of the terminating resistors, and the value utilized for R can be adjusted based on empirical tests or computations to take the terminating resistors into account. Thus, using sensing resistors of 100 Ohms in the circuit, we have modified expression (18) to use a value for R of 102 Ohms in one case, and 107 Ohms in another case, and those values have rendered the core determination more accurate in the presence of terminating resistors.

Figure 9:
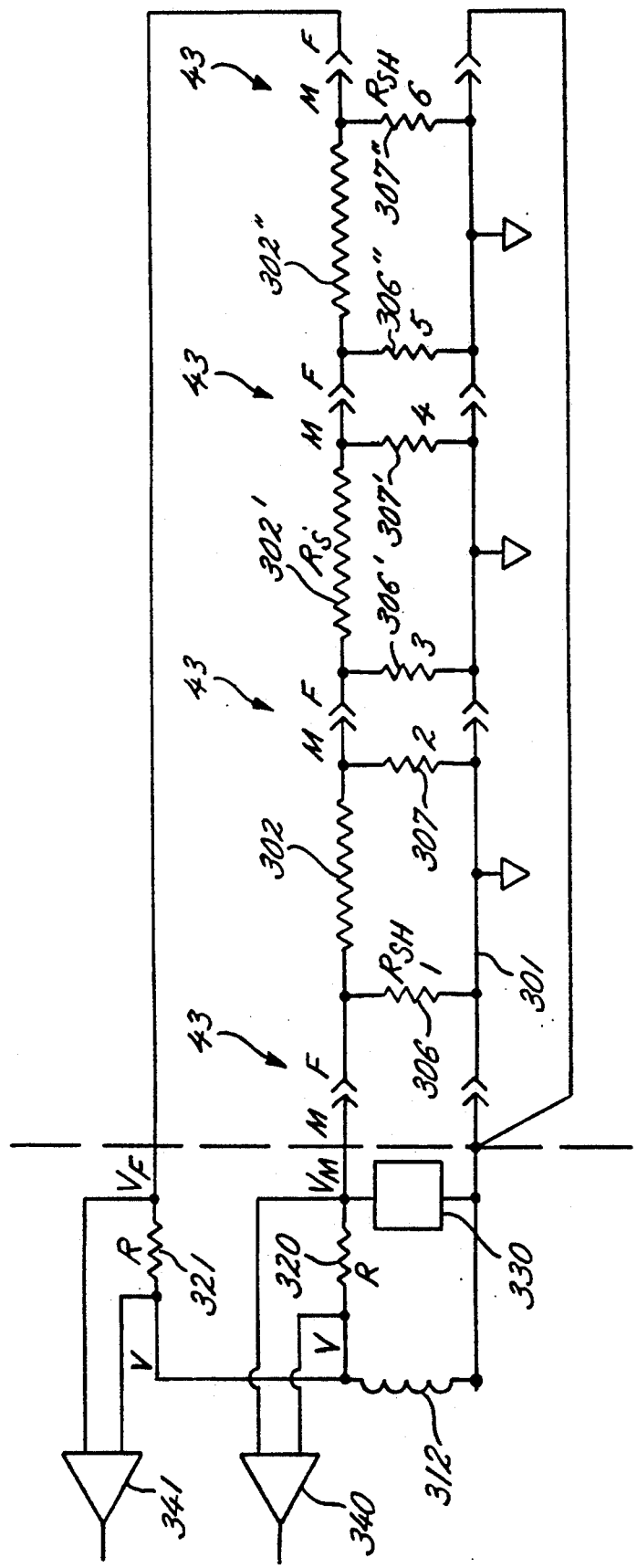
FIG. 9 is a simplified circuit diagram showing the manner in which the cable terminating resistors provide for sensing of a disconnected or broken cable.

Turning to the terminating resistors themselves, it was noted above that they are used for sensing breaks in the cable. The manner in which that is accomplished is better illustrated in connection with FIG. 9. FIG. 9 shows an elongate sensor cable configured in a loop, with a plurality of core resistances 302, 302', 302" connected in series by way of connectors 43. The male and female ends of the connectors are denoted by the M and F designators in the drawing. The sensor is connected in a loop, with the core connector being driven by the secondary 312 of the driving transformer through sensing resistors 320, 321. The nomenclature $V_m$ indicates the voltage measured at the junction of the sensing resistor 320 and the male end of the sensing table, and the designator $V_F$ indicates the voltage measured at the junction between the sensing resistor 321 and the female end of the sensing cable. The designator V indicates the voltage at the secondary 312. The box designated 330 indicates the switch which shunts the male end of the core to the grounded end of the secondary in order to impose the signal of the secondary 312 across the total core resistance. The shunt or terminating resistors 306, 307 are shown associated with each connector, resistors 306 and 307 being shown at the respective end of core resistance 302, shunt resistances 306', 307' being shown associated with core resistance 302', etc.

The amplifiers 340, 341 are shown sensing the voltage drop across sensing resistors 320, 321, and it is those amplifiers or their equivalent which are used to determine any breaks in the cable by sensing the resistance of shunt resistors 306, 307. The determination is made in the terms of the number of shunt resistances seen from the male, or from the female end of the cable loop, and thus it will be seen that the procedure is capable of locating two breaks in the cable. It will also be appreciated that the procedure is capable of locating not only open connectors 43, but actual breaks in the cable itself.

The number of shunt resistors seen from the female and under conditions of a cable break is the determined from the following expression:

$$N_F = \frac{(R_{SH} + R)}{R} \frac{(V - V_F)}{V} \quad (19)$$

Where $N_F$ is the number of shunt resisted measured by the circuit starting at the female end of the cable, $R_{SH}$ is the value of each shunt resistor, and the other variables are as previously described. The computation is, of course, rounded-off to the nearest whole number to determine the number of terminating resistors encountered to the break. Similarly, the number of terminating resistors to a cable break when measured from the male end of the cable is determined by the following expression:

$$N_M = \frac{(R_{SH} + R)}{R} \frac{(V - V_M)}{V} \quad (20)$$

The number is again rounded-off to the nearest whole number, and yields the number of shunt resistors encountered between the male end of the cable and a break in the cable.

It will thus be apparent that a test can be performed to determine the resistance of the core, i.e., by turning on transistor 330 and measuring the resistance of the core by expression (18). If that test indicates that there is a break in the core, the transistor 330 can be turned off and measurements taken from the female and male end, and expressions 19 and 20 utilized to determine the number of shunt resistors from each end to the break. That computation may determine that there is only one break in the cable, and the maintenance crew will know exactly where it is. If there is two breaks in the cable, the position of both will be located.

Other conditions can be monitored by means of sensing the currents through the sensing resistors 320, 321. For example, if either or both of the currents through those resistors is zero, it will be determined that there is a circuit failure. A lower level for total current $I_1 + I_2$ can be established, and that will establish an upper level for the total resistance of the loop. If that total resistance is exceeded, the system will determine that the sensor loop is open.

In addition, the system functionality can be determined by energizing the test transistor periodically and determining the sensor resistance. If the sensor resistance is determined to be between certain limits, such as greater than 3 Ohms and less than 100 Ohms, it can be determined that the sensor is in place and the system is functional. Finally, in any case where $I_1$ is found to be greater than or equal to $I_2$, with the test transistor on, that will be found to be a circuit failure, since that is not a possible condition.

It will now be appreciated that what has been provided is an improved resistive sensor used as the sensing component in a pneumatic manifold fault detection system. The system operates on resistive principles and thus is substantially EMI resistant, at least more so than those which utilize capacitive bridges, for example. The system is capable of locating very localized faults in that only a very small section of the cable need be heated in order to cause a breakdown of the eutectic insulator, and provide differential current signals in the resistive sensor measured and in the sensing manipulated as described herein to produce an indication of the position of the fault.

What is claimed is:

1. A sensor for determining the location of overtemperature conditions, the sensor comprising, in combination:
   an elongate coaxial sensor cable having a conductive metallic sheath and a conductive metallic core both made of metals capable of withstanding, without failure, the heat of the overtemperature condition, the core being positioned within and coaxial with the sheath, the elongate cable being sufficiently flexible to be routed in proximity to a system to be monitored,
   a eutectic salt insulator interposed between the core and sheath for preventing contact therebetween, the eutectic salt having a melting point related to a design temperature at which the overtemperature condition is to be detected,
   at least one of the core or sheath having a predetermined and measurable resistance per unit length sufficiently high to allow differential drive and sensing from the respective cable ends to isolate the position of a core-to-sheath short,
   the eutectic salt insulator being constructed such that when heated to the design temperature at a point of overtemperature condition it provides a core-to-sheath short at said position rendering the core-to-sheath resistance determined by differential driving and sensing the cable from its respective ends an indication of the position of the short along the cable.

2. The sensor as set forth in claim 1 wherein fittings are provided at the ends of the cable, the fittings being affixed to the cable to provide a core-to-sheath seal at the ends of the cable, thereby to prevent moisture ingress into the eutectic salt.

3. The sensor as set forth in claim 1 wherein the core has a predetermined measurable resistance per unit length, and the sheath is substantially resistance-free, whereby the core is adapted for driving at the respective ends to sense differential current at the ends as a measure of the position of the core-to-sheath short.

4. The sensor as set forth in claim 3 wherein the sensor cable is configured in a loop for driving and sensing at the respective ends so as to determine the location of any fault caused by a local overtemperature condition.

5. The sensor as set forth in claim 1 wherein the sensor comprises a plurality of individual sensor lengths, connectors attached to the ends of the lengths for joining the lengths end-to-end to form a sensor loop of desired length.

6. The sensor as set forth in claim 5 further comprising terminating resistors associated with the connectors, the terminating resistors being mechanically and electrically connected from core to sheath, and having resistance about an order of magnitude greater than the total resistance of the core and cladding combination, thereby to afford the ability to locate breaks in the sensor.

7. The sensor as set forth in claim 6 wherein each terminating resistance is a resistive disk affixed to the connector assembly at the ends thereof and making a mechanical and electrical connection between core and sheath.

8. The sensor as set forth in claim 5 wherein the connectors provide an hermetic seal at the ends of each length, thereby to prevent moisture ingress into the eutectic salt.

9. The sensor as set forth in claim 8 wherein each connector includes a ceramic insert having an aperture for allowing passage of the core, and providing a core-to-sheath seal for excluding moisture from the eutectic salt.

10. The sensor as set forth in claim 1 wherein the core and sheath are made of nickel or an alloy having a high nickel content to provide a temperature-resistive cable capable of withstanding the temperature of the overtemperature condition.

11. The sensor as set forth in claim 10 wherein the core has a resistivity of about 15 Ohms per meter or more.

12. The sensor as set forth in claim 11 wherein the outer diameter of the sheath is no more than about 2 millimeters thereby to provide a thin but rugged cable capable of sensing overtemperature conditions without adding substantial weight to the monitored system.

* * * * *

UNITED STATES PATENT AND TRADEMARK OFFICE
CERTIFICATE OF CORRECTION

PATENT NO. : 5,294,909
DATED : March 15, 1994
INVENTOR(S) : Glenn E. Frazier

It is certified that error appears in the above-indentified patent and that said Letters Patent is hereby corrected as shown below:

Column 5, line 68, change "sheath 4" to read -- sheath 40 --.

Column 6, line 52, change "core 4" to read -- core 41 --.

Column 12, line 28, change "loop R" to read -- loop $R_S$ --.

Column 12, line 33, change "I and I:" to read
-- $I_1$ and $I_2$ --.

Column 15, line 5, change "I:" to read -- $I_2$ --.

Signed and Sealed this

Fifteenth Day of November, 1994

Attest:

BRUCE LEHMAN

*Attesting Officer*     *Commissioner of Patents and Trademarks*